United States Patent
Bar-Shalom (10) Patent No.: US 7,883,722 B2
(45) Date of Patent: Feb. 8, 2011

(54) CONTROLLED RELEASE COMPOSITION

(75) Inventor: Daniel Bar-Shalom, Kirke Værløse (DK)

(73) Assignee: Egalet Ltd., London (GB)

( * ) Notice: Subject to any disclaimer, the term of this patent is extended or adjusted under 35 U.S.C. 154(b) by 0 days.

(21) Appl. No.: 10/845,522

(22) Filed: May 14, 2004

(65) Prior Publication Data

US 2005/0089569 A1 Apr. 28, 2005

Related U.S. Application Data

(63) Continuation of application No. 09/647,590, filed as application No. PCT/DK99/00174 on Mar. 25, 1999, now abandoned.

(30) Foreign Application Priority Data

Apr. 3, 1998 (EP) .................................. 98610009

(51) Int. Cl.
| | |
|---|---|
| *A61K 9/14* | (2006.01) |
| *A61K 9/44* | (2006.01) |
| *A61K 9/22* | (2006.01) |

(52) U.S. Cl. .................. 424/486; 424/467; 424/468
(58) Field of Classification Search .................. 424/486, 424/473, 485, 488, 468
See application file for complete search history.

(56) References Cited

U.S. PATENT DOCUMENTS

| | | | |
|---|---|---|---|
| 4,330,338 A | 5/1982 | Banker | |
| 4,389,393 A | 6/1983 | Schor et al. | |
| 4,824,675 A | 4/1989 | Wong et al. | |
| 4,844,984 A | 7/1989 | Eckenhoff et al. | |
| 4,873,080 A | 10/1989 | Brickl et al. | |
| 4,892,742 A | 1/1990 | Shah | |

(Continued)

FOREIGN PATENT DOCUMENTS

| | | |
|---|---|---|
| DE | 2332484 | 6/1972 |
| DE | 2415490 | 4/1973 |
| EP | 0 908 181 | 4/1999 |
| EP | 0 335 560 | 1/2002 |
| EP | 1 371 360 | 5/2005 |

(Continued)

OTHER PUBLICATIONS

The Condensed Chemical Dictionary, 9th edition, p. 584, 1977.*

(Continued)

*Primary Examiner*—Blessing M Fubara
(74) *Attorney, Agent, or Firm*—Foley & Lardner LLP (57) ABSTRACT

A composition for controlled delivery of at least one active substance into an aqueous medium by erosion at a preprogrammed rate of at least one surface of the composition, the composition comprising a matrix which is erodible in the aqueous medium in which the composition is to be used and which allows substantially no diffusion of water into the composition beyond any exposed surface layers of the matrix, the matrix comprising at least one substantially water soluble crystalline polymer, e.g. a polyethylene glycol, with at least one water-dispersible or water-soluble surface active agent, e.g. a non-ionic emulsifier, dispersed therein, at least one release modifier, e.g. an enteric coating material, that functions to regulate erosion of the matrix within a pH range of from about 2 to about 7, and at least one active substance. The composition provides controlled, e.g. substantially zero order, release in both the stomach and the intestines despite different conditions of pH, agitation and absorption.

16 Claims, 2 Drawing Sheets

U.S. PATENT DOCUMENTS

| | | | |
|---|---|---|---|
| 4,898,733 | A | 2/1990 | De Prince et al. |
| 5,068,112 | A | 11/1991 | Samejima et al. |
| 5,102,668 | A * | 4/1992 | Eichel et al. ............... 424/490 |
| 5,213,808 | A * | 5/1993 | Bar-Shalom et al. ........ 424/473 |
| 5,419,917 | A | 5/1995 | Chen et al. |
| 5,422,123 | A | 6/1995 | Conte et al. |
| 5,478,577 | A | 12/1995 | Sackler et al. |
| 5,618,560 | A | 4/1997 | Bar-Shalom et al. |
| 5,683,719 | A | 11/1997 | Newton |
| 5,741,524 | A | 4/1998 | Staniforth et al. |
| 5,814,336 | A * | 9/1998 | Kelm et al. ................. 424/463 |
| 6,395,299 | B1 | 5/2002 | Babich et al. |
| 6,465,626 | B1 * | 10/2002 | Watts et al. .................... 536/20 |
| 6,488,962 | B1 | 12/2002 | Berner et al. |
| 6,517,866 | B1 | 2/2003 | Am Ende et al. |
| 6,534,085 | B1 | 3/2003 | Zeligs |
| 6,562,375 | B1 | 5/2003 | Sako et al. |
| 6,709,678 | B2 | 3/2004 | Gruber |
| 6,787,156 | B1 | 9/2004 | Bar-Shalom |
| 2001/0036959 | A1 | 11/2001 | Gabel et al. |
| 2002/0054911 | A1 | 5/2002 | Oh |
| 2003/0035836 | A1 | 2/2003 | Shanghvi et al. |
| 2004/0151772 | A1 | 8/2004 | Andersen et al. |
| 2004/0213849 | A1 | 10/2004 | Sowden et al. |
| 2004/0234602 | A1 | 11/2004 | Fischer et al. |
| 2004/0253310 | A1 | 12/2004 | Fischer et al. |
| 2005/0019399 | A1 | 1/2005 | Fischer et al. |
| 2005/0019405 | A1 | 1/2005 | Bar-Shalom |
| 2005/0163837 | A1 | 7/2005 | Boehm et al. |
| 2007/0003617 | A1 | 1/2007 | Fischer et al. |
| 2007/0042044 | A1 | 2/2007 | Fischer et al. |
| 2008/0234352 | A1 | 9/2008 | Fischer et al. |
| 2008/0254122 | A1 | 10/2008 | Fischer et al. |
| 2008/0254123 | A1 | 10/2008 | Fischer et al. |
| 2008/0254124 | A1 | 10/2008 | Bar-Shalom |
| 2008/0268057 | A1 | 10/2008 | Andersen et al. |
| 2009/0274759 | A1 | 11/2009 | Bar-Shalom et al. |

FOREIGN PATENT DOCUMENTS

| | | | |
|---|---|---|---|
| GB | 2170104 | | 7/1986 |
| GB | 2182559 | | 5/1987 |
| JP | 60-255719 | * | 12/1985 |
| JP | 07-1001 | * | 4/1995 |
| WO | WO 86/04817 | | 8/1986 |
| WO | WO 89/09066 A1 | | 10/1989 |
| WO | WO 90/08536 | | 8/1990 |
| WO | WO 91/04015 A1 | | 4/1991 |
| WO | WO 92/09270 | | 6/1992 |
| WO | WO 95/22962 | * | 8/1995 |
| WO | WO 95/22962 A1 | | 8/1995 |
| WO | WO 9522962 | * | 8/1995 |
| WO | WO 99/44591 | | 9/1999 |
| WO | WO 99/51208 | | 10/1999 |
| WO | WO 01/35958 | | 5/2001 |
| WO | WO 01/51035 | | 7/2001 |
| WO | WO 01/51036 | | 7/2001 |
| WO | WO 01/74357 | | 10/2001 |
| WO | WO 02/065834 | | 8/2002 |
| WO | WO 02/092078 | | 11/2002 |
| WO | WO 2005/007074 | | 1/2005 |
| WO | WO 2005/027878 | | 3/2005 |

OTHER PUBLICATIONS

Bravo et al. in J. Pharmaceutical Science, vol. 5, #3, pp. 213-219, 2002.*
Marvola et al. ("Enteric polymers as binders and coating materials in multiple-unit site specific drug delivery systems," in European Journal of Pharmaceutical Sciences, Feb. 1999, No. 7, 259-267).*
J. Varshosaz , *, R. A. Kennedy and E. M. Gipps, "Use of enteric polymers for production of microspheres by extrusion-spheronization," in Pharmaceutica Acta Helvetiae vol. 72, Issue 3, Jun. 1997, pp. 145-152.*
Giunchedi et al., "Hydorphilic Matrices for the Extended Release of a Model Drug Exhibiting Ph-dependent Solubility," *International Journal of Pharmaceutics*, 1992, pp. 141-147, vol. 85.
Yamakita et al., "In Vitro Vivo Evaluation of Two Series of TA-5707F Controlled Release Matrix Tablets Prepared with Hydroxypropyl Methyl Cellulose Derivatives with Entero-Soluble or Gel Formation Properties," *Biological & Pharmaceutical Bulletin*, 1995, pp. 1409-1416, vol. 18, No. 10.
U.S. Appl. No. 11/915,655, filed Nov. 27, 2007, Bar-Shalom et al.
Hoshi et al., Cellulose and its Derivatives, pp. 24-25 (1992).
Miyazaki et al., "In situ-gelling gellan formulations as vehicles for oral drug delivery," *J. Control Release*, vol. 60, pp. 287-295 (1999).
Rowe et al., *Handbook of Pharmaceutical Excipients*, Pharmaceutical Presse, $4^{th}$ edition, pp. 257-258 (2003).
WWW.WIKIPEDIA.ORG, web page on phosphoric acid.
Office Action issued Oct. 24, 2006 by the Examiner in U.S. Appl. No. 10/703,084, (US 2004/0151772).
Office Action issued Jun. 14, 2007 by the Examiner in U.S. Appl. No. 10/703,084, (US 2004/0151772).
Office Action issued Aug. 3, 2006 by the Examiner in U.S. Appl. No. 10/490,169, (US 2004/0253310).
Office Action issued Mar. 2, 2007 by the Examiner in U.S. Appl. No. 10/490,169, (US 2004/0253310).
Office Action issued Dec. 20, 2007 by the Examiner in U.S. Appl. No. 10/827,521, (US 2004/0019405).
Office Action issued Jul. 25, 2006 by the Examiner in U.S. Appl. No. 10/490,308, (US 2004/0234602).
Office Action issued Mar. 9, 2007 by the Examiner in U.S. Appl. No. 10/490,308, (US 2004/0234602).
Office Action issued Oct. 3, 2006 by the Examiner in U.S. Appl. No. 10/490,170, (US 2005/0019399).
Office Action issued May 9, 2007 by the Examiner in U.S. Appl. No. 10/490,170, (US 2005/0019399).
Office Action issued Oct. 22, 2002 by the Examiner in U.S. Appl. No. 09/647,590.
Office Action issued May 11, 2001 by the Examiner in U.S. Appl. No. 09/647,590.
Office Action issued Jul. 14, 2003 by the Examiner in U.S. Appl. No. 09/647,590.
Office Action issued Jan. 30, 2002 by the Examiner in U.S. Appl. No. 09/647,590.
Office Action issued Dec. 15, 2008 by the Examiner in U.S. Appl. No. 12/213,087 (US 2008/0254124).
Office Action issued Dec. 23, 2008 by the Examiner in U.S. Appl. No. 10/550,685 (US 2007/0042044).
Office Action issued Jun. 17, 2009 by the Examiner in U.S. Appl. No. 10/550,685 (US 2007/0042044).
Office Action issued on Aug. 5, 2010 by the Examiner in U.S. Appl. No. 10/550,453 (US 2007/0003617).
Office Action issued on Apr. 13, 2010 by the Examiner in U.S. Appl. No. 10/550,453 (US 2007/0003617).
Office Action issued on Nov. 10, 2009 by the Examiner in U.S. Appl. No. 10/550,453 (US 2007/0003617).
Office Action issued on Jun. 16, 2009 by the Examiner in U.S. Appl. No. 10/550,453 (US 2007/0003617).
Office Action issued on Mar. 1, 2010 by the Examiner in U.S. Appl. No. 10/550,685 (US 2007/0042044).
Office Action issued on Jun. 17, 2009 by the Examiner in U.S. Appl. No. 10/550,685 (US 2007/0042044).
Office Action issued on Jun. 18, 2010 by the Examiner in U.S. Appl. No. 12/076,105 (US 2008/0268057).
Office Action issued on Sep. 29, 2009 by the Examiner in U.S. Appl. No. 12/076,105 (US 2008/0268057).
Office Action issued on Dec. 23, 2008 by the Examiner in U.S. Appl. No. 10/550,685 (US 2007/0042044).
Office Action issued on Apr. 29, 2009 by the Examiner in U.S. Appl. No. 12/076,105 (US 2008/0268057).

* cited by examiner

CONTROLLED RELEASE COMPOSITION

This application is a continuation of application Ser. No. 09/647,590 filed Dec. 12, 2000, now abandoned, which is a 371 of PCT/DK99/00174 filed Mar. 25, 1999, which claims priority to European Patent Application number 98610009.7 filed Apr. 3, 1998.

FIELD OF THE INVENTION

The present invention relates to controlled release compositions for delivery of an active substance into an aqueous medium, the compositions being designed so as to regulate release of the active substance at the different pH values found in the gastrointestinal tract.

BACKGROUND OF THE INVENTION

Numerous compositions for controlled release of an active substance, e.g. a pharmaceutically active powder, into an aqueous medium, e.g. the human gastrointestinal tract, are known. Such controlled release may for example be obtained by embedding the active substance in a matrix of an insoluble substance from which the active substance will gradually diffuse. Sustained release of an active substance contained in a tablet core may also be achieved by applying to the core a semi-permeable coating through which water and dissolved active substance may diffuse or an insoluble coating provided with a hole through which the active substance is released. Gradual release of an active substance may furthermore be obtained by microencapsulating particles of an active substance in one or more layers of film which may be of various types, e.g. of a type which mediates diffusion of the active substance or release thereof in the intestines.

WO 89/09066 discloses a composition for controlled delivery of an active substance into an aqueous phase by erosion at a substantially constant rate of a surface or surfaces of the composition, the composition containing a) a matrix of a crystalline polyethylene glycol (PEG) polymer with a molecular weight of at least 20,000 daltons, b) at least one non-ionic emulsifier dispersed in the polyethylene glycol matrix in an amount of 2-50% by weight of the crystalline polymer and the non-ionic emulsifier, the non-ionic emulsifier having at least one domain which is compatible with the polyethylene glycol polymer and being selected from fatty acid esters and fatty alcohol ethers, and c) at least one active substance substantially homogeneously dispersed in the polyethylene glycol matrix and/or located in geometrically well-defined zones within the composition, the non-ionic emulsifier and/or the active substance reducing the water affinity of domains between grains and in cracks in the crystalline polymer matrix and in the crystalline polymer matrix itself, thereby substantially eliminating water diffusion in the interface between the polymer crystals, so that the erosion is predominantly effected by the dissolving action of an aqueous medium on a surface or surfaces of the composition exposed to the medium.

Other controlled release compositions based on this principle are disclosed in WO 91/04015, which relates to compositions that provide a regulated non-initial burst release of an active substance at a predetermined time.

WO 95/22962 describes controlled release compositions with a matrix of the type described in WO 89/09066, the compositions being further provided with a cellulose derivative-based coating having at least one opening exposing at least one surface of the matrix, the coating being one which crumbles and/or erodes upon exposure to the aqueous medium at a rate which is equal to or slower than the rate at which the matrix erodes in the aqueous medium. This allows exposure of the surface of the matrix to the aqueous medium to be controlled.

U.S. Pat. No. 5,683,719 describes controlled release compositions in the form of extruded rods or tubes comprising an active material, microcrystalline cellulose and clay, the rods or tubes being coated with a material allowing dissolution of the active material to proceed in a controlled manner and allowing the rods or tubes to retain their structural integrity during the release period.

While the known controlled release compositions such as those described above provide great advantages in terms of allowing controlled, e.g. zero order, delivery of an active substance or release of an active substance according to a predetermined pattern, certain problems are nevertheless encountered in connection with oral delivery of active substances in this manner due to the very substantial differences in the chemical and physical environment found in different parts of the gastrointestinal system. Especially when a constant zero order release of an active substance is desired, one is faced with the problem that the composition first passes through the stomach, which has a very low pH, typically about 2, together with a high degree of agitation due to peristaltic movements and the presence of a relatively large amount of low viscosity liquids, and then to the intestines, which have a substantially neutral pH of about 7 and a low degree of agitation. A further complication in this regard is the fact that the absorption capability of the stomach is in many cases different from, typically much greater than, that of the intestines. As a result of these two factors, the delivery rate of an active substance when a given controlled release composition is present in the stomach is normally several times greater than the delivery rate for the same composition when it is present in the intestines. This is obviously a significant disadvantage when zero order release is desired over an extended period of time, i.e. several hours. An additional problem is that the residence time of a composition in the stomach can vary tremendously, e.g. from about 1 hour to about 4 hours or more. Thus, providing zero order release by merely adapting part of a controlled release composition for a given release rate under a given set of conditions in the stomach and another part of the composition for a different release rate under another set of conditions in the intestines is not possible as such, because there is no way of knowing in advance what the residence time in the stomach will be in any given case.

The present invention is a further development based on the inventions disclosed in WO 89/09066, WO 91/04015 and WO 95/22962. In particular, it has surprisingly been found that it is possible to regulate the release profile of these and similar controlled release compositions containing an active substance by incorporating into the matrix a release modifier that functions to regulate erosion of the matrix in the acidic pH range found in the stomach, while at the same time allowing release of the active substance after the composition reaches the intestines.

BRIEF DISCLOSURE OF THE INVENTION

One aspect of the invention thus relates to a composition for controlled delivery of at least one active substance into an aqueous medium by erosion at a preprogrammed rate of at least one surface of the composition, the composition comprising a matrix which is erodible in the aqueous medium in which the composition is to be used and which allows substantially no diffusion of water into the composition beyond any exposed surface layers of the matrix, the matrix comprising at least one substantially water soluble crystalline polymer with at least one water-dispersible or water-soluble surface active agent dispersed therein, at least one release modifier that functions to regulate erosion of the matrix within a pH range of from about 2 to about 7, and at least one active substance.

Another aspect of the invention relates to a method for producing a composition for controlled delivery of at least one active substance into an aqueous medium by erosion at a preprogrammed rate of at least one surface of the composition, the method comprising forming, e.g. by means that include extrusion, injection moulding, blow moulding or compression moulding, a matrix which is erodible in the aqueous medium in which the composition is to be used and which allows substantially no diffusion of water into the composition beyond any exposed surface layers of the matrix, the matrix comprising at least one substantially water soluble crystalline polymer with at least one water-dispersible or water-soluble surface active agent dispersed therein, at least one release modifier that functions to regulate erosion of the matrix within a pH range of from about 2 to about 7, and at least one active substance, and optionally providing a coating having at least one opening exposing at least one surface of said matrix.

A further aspect of the invention relates to a method for regulating release of an active substance from a controlled release composition in the small intestine relative to release of the same active substance from the same composition in the large intestine, based on differences in pH between the small and large intestines, by adapting the concentration of the release modifier and/or the active substance in at least one zone of the composition so as to obtain a first release rate of the active substance in the small intestine and a second release rate of the active substance in the large intestine.

Further aspects and preferred embodiments of the invention will be apparent from the discussion below.

DETAILED DISCLOSURE OF THE INVENTION

In a preferred embodiment, the composition of the invention is one wherein release of the active substance is adapted so that the release rate in an in vitro dissolution method corresponding to the environment of the human stomach with respect to peristaltic movements and pH as described below is not substantially greater than the release rate of the active substance in an in vitro dissolution method corresponding to the environment of the human intestines with respect to peristaltic movements and pH as described below.

The term "not substantially greater" in this context refers to the fact that the release rate in the dissolution method corresponding to the environment of the human stomach preferably lies within the range of about 25-250% of the release rate of the dissolution method corresponding to the environment of the human intestines. The release rate in the stomach will thus often be somewhat higher than that of the intestines, but may in certain cases be somewhat lower. In general, however, the release rate in the stomach will preferably be not more than about 250% of the release rate in the intestines, more preferably not more than about 200%, such as not more than about 150%. Similarly, the release rate in the stomach will generally not be less than about 50% of the release rate in the intestines, preferably not less than about 60%, e.g. not less than about 75%.

Preferably, the substantially water soluble crystalline polymer of the matrix comprises a crystalline polyethylene glycol polymer having dispersed therein at least one non-ionic emulsifier as the surface active agent. A suitable matrix for use in the compositions of the invention is one of the type described in WO 89/09066 or WO 91/04015, to which reference is made and which are incorporated herein by reference, i.e. a matrix containing a crystalline polyethylene glycol polymer, typically with a molecular weight of at least about 20,000 daltons, in which at least one non-ionic emulsifier is dispersed. Suitable non-ionic emulsifiers include e.g. fatty acid esters and/or fatty acid ethers, for example a fatty acid ester and/or fatty acid ether having carbon chains of from 12 to 24 carbon atoms, typically from 12 to 20 carbon atoms, such as an ester and/or ether of palmitic acid or stearic acid. Examples are polyglycol esters and ethers, polyethylene glycol esters and ethers, polyhydroxy esters and ethers, and sugar esters and ethers such as a sorbitan ester or ether. A suitable HLB (hydrophilic-lipophilic balance) value is in the range of from about 4 to about 16. The non-ionic emulsifier is preferably approved for use in products to be ingested by humans or animals, i.e. pharmaceuticals and/or foodstuffs. A preferred non-ionic emulsifier for use in the matrix is polyethylene glycol stearate, in particular a polyethylene glycol monostearate such as polyethylene glycol 400 or 2000 monostearate. Tartaric acid, citric acid and lactic acid esters of mono- and diglycerides, as well as fatty acid esters of glycerol may also be employed. The matrix may in addition include a cellulose derivative, e.g. a cellulose derivative selected from the group consisting of methylcellulose, carboxymethylcellulose and salts thereof, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose. Of these cellulose derivatives, hydroxypropylmethylcellulose and methylcellulose are preferred for incorporation in the matrix.

Although the amount of surface active agent will vary depending on such factors as the nature of the surface active agent and the desired dissolution characteristics of the matrix, the surface active agent will typically be present in an amount of about 1-40% by weight of the matrix, more typically about 2-30%, e.g. about 4-20%, such as about 5-15%.

Preferred crystalline polyethylene glycol polymers for use in the matrix have a molecular weight in the range of 20,000-35,000 daltons, although interesting compositions according to the present invention will also include those in which the matrix contains a polyethylene glycol polymer with a molecular weight of less than 20,000 daltons, e.g. in the range of about 10,000-20,000 daltons.

The crystalline polymer matrix must have a melting point which is above the temperature of the aqueous medium in which the composition of the invention is to be used. Thus, for the delivery of a drug for human or veterinary use, the matrix will suitably have a melting point of about 40-80° C.

Where reference is made herein to the fact that the release modifier functions to regulate erosion of the matrix within a pH range of from about 2 to about 7, this means that the release modifier is one which, due to its pH-dependent solubility, provides the matrix with different degrees of erosion at different pH values within this range. Typically, the release modifier will be a compound that is soluble above a given pH in the range of from about 5 to about 7, e.g. a pH of about 5.0, 5.5, 6.0, 6.5 or 7.0, but substantially insoluble at lower pH values.

The release modifier is preferably selected from materials conventionally used in the pharmaceutical industry to produce enteric coatings. A number of different types of compounds suitable for use as enteric coatings are known in the art; see e.g. *Remington's Pharmaceutical Sciences*, 18th Edition, 1990. Release modifiers may in particular be selected from one of three general classes, namely cellulose derivatives, methacrylic acid polymers and modified gelatine compounds. Preferred release modifiers include cellulose acetate phthalate, polyvinyl acetate phthalate, hydroxypropyl methylcellulose phthalate and hydroxypropyl methylcellulose acetate succinate, as well as methacrylic acid copolymers. Modified gelatine compounds include gelatine treated with e.g. formaldehyde or glutaraldehyde. Examples of commercially available polymers suitable as release modifiers are EUDRAGIT® L and EUDRAGIT® S, available from Röhm GmbH, Germany, and enteric coating agents available from Shin-Etsu Chemical Co., Japan. The release modifier will typically be present in the composition in an amount of about 0.1-10%, based on the weight of the matrix, preferably about 0.5-4%, e.g. about 1-3%, such as about 1.5-2.0%. If desired, a suitable mixture of more than one release modifier may be used in order to obtain a desired release profile in any given composition.

In a preferred embodiment, the controlled release composition of the invention further comprises a coating having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled. Coatings of this type are described in WO 95/22962, to which reference is made and which is incorporated herein by reference. These coatings comprise:
  (a) a first cellulose derivative which has thermoplastic properties and which is substantially insoluble in the aqueous medium in which the composition is to be used, e.g. an ethylcellulose such as ethylcellulose having an ethoxyl content in the range of 44.5-52.5%, or cellulose acetate, cellulose propionate or cellulose nitrate; and at least one of:
  (b) a second cellulose derivative which is soluble or dispersible in water, e.g. a cellulose derivative selected from the group consisting of methylcellulose, carboxymethylcellulose and salts thereof, cellulose acetate phthalate, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose;
  (c) a plasticizer, e.g. selected from the group consisting of phosphate esters; phthalate esters; amides; mineral oils; fatty acids and esters thereof with polyethylene glycol, glycerin or sugars; fatty alcohols and ethers thereof with polyethylene glycol, glycerin or sugars; and vegetable oils; or a non-ionic surfactant; and
  (d) a filler, e.g. selected from conventional tablet or capsule excipients such as diluents, binders, lubricants and disintegrants.

A coating of this type may in addition further comprise a release modifier of the type described above, so that the coating is provided with an erosion profile similar to that of the matrix in terms of the relative rate of erosion in the stomach and the intestines, respectively. In this case, it may be advantageous to incorporate a somewhat higher concentration of the release modifier in the coating than the concentration of release modifier in the matrix, so as to ensure that the coating does not erode in the stomach at a faster rate than the matrix.

In a further preferred embodiment, the composition of the invention will be adapted to compensate for differential absorption in the gastrointestinal tract or to provide different rates of release of the active substance in the small intestine and in the large intestine, e.g. by varying the concentration of the release modifier or the active ingredient in different zones of the matrix. The exact release profile provided by any given matrix in a controlled release composition of the invention will of course be dependent on the nature of the matrix, including the type and amount of crystalline polymer, surface active agent and release modifier, as well as the nature and amount of the active ingredient in the matrix and the characteristics of a possible coating. However, by adjusting in particular the concentration of the release modifier and the active ingredient, and using routine testing of appropriate variations in vitro and in vivo, a person skilled in the art will readily be able to arrive at compositions that provide a desired release profile for a given active substance under a given set of circumstances.

For example, for obtaining a composition with a first release rate in the small intestine and a second release rate in the large intestine (the small intestine typically having a slightly higher pH value than the large intestine, i.e. normally about 7.2 and 6.9, respectively), a release modifier which is soluble at a pH of from about 7.0 or 7.1, but which is substantially insoluble or at least substantially less soluble at pH values below 7.0, may be chosen. In this case, the composition will comprise at least one first zone with a first concentration of the release modifier and optionally at least one second zone with a second concentration of the release modifier. An example of a suitable release modifier for this purpose is EUDRAGIT® S, available from Röhm GmbH, Germany.

In many cases, it will be preferred that the active substance is substantially homogeneously distributed throughout the matrix. A matrix of this type will be simpler to produce, and for many purposes a simple release profile obtained in this manner will be sufficient. In other cases, however, it will be desired to have at least two matrix zones having different concentrations of the active substance, since this makes it possible to provide more complex release profiles, for example a pulsatile or second burst release of the active substance. Many different variations on such a composition can of course be contemplated, e.g. a composition comprising, in addition to at least one matrix zone comprising an active substance, at least one remote zone comprising an active substance, optionally dispersed in a filler, such that the remote zone becomes exposed to the aqueous medium after a predetermined period of at least about 15 minutes after administration of the composition. These types of more complex compositions may also include two or more different active substances in two or more different zones of the composition. Different release patterns (i.e. zero order and pulsatile) may also be combined so that a uniform release of one active substance (for example at a fairly low dosage level) alternates with the release in bursts of the same or another active substance (for example at a higher dosage level). Other variations will be apparent to persons skilled in the art.

Due to the nature of the matrix, diffusion of water into the composition of the invention is substantially limited to any exposed surface layers of the matrix, and release of the active substance is therefore proportional to the rate of erosion of such exposed matrix surfaces. Since the present invention makes it possible to adapt the erosion rate taking into consideration the different pH, agitation, absorption and residence time conditions existing in the stomach and intestines, the release profile of any given composition can similarly be adapted as necessary. In particular, the invention makes it possible to obtain an approximately zero order release profile over an extended period of time, e.g. up to about 24 hours or even longer, in spite of the significantly different conditions to which a composition is exposed during such an extended time period while passing through the various portions of the gastrointestinal system. This is obviously a tremendous advantage, and one which greatly improves the utility and range of possible uses for such controlled release compositions.

In a preferred version of the invention, the composition has a geometric shape which enables a substantially constant surface area to become exposed during erosion of the matrix. This may, for example, be a cylindrical rod provided with a cellulose derivative-based coating of the type described above, the coating having an opening at one or both ends. The term "cylindrical rod" as used in this context should be understood to comprise not only those geometrical forms having a substantially circular cross-section, but also other substantially cylindrical forms, e.g. those having a somewhat flattened cross-section, for example a substantially oval or ellipse shaped cross-section. It will also be understood by a person skilled in the art that the specific finished form of the composition of the invention may comprise certain minor modifications in order to facilitate the use of the composition in question. For example, a cylindrical rod-shaped composition for delivery of a pharmaceutical powder may have rounded ends so as to avoid possible injury or discomfort when the composition is introduced into the body.

The active substance to be delivered by the controlled release compositions of the invention is in particular a biologically active substance for which a continuous or otherwise controlled release in an aqueous environment is desired, for example a drug for human or veterinary use, or a vitamin or other nutritional supplement. The compositions are especially suitable for the delivery of a pharmaceutically active substance, in particular a pharmaceutically active powder, to humans or animals. The pharmaceutically active substance or substances included in the compositions of the invention may be selected from a wide range of therapeutic categories, in particular from substances which may advantageously be administered orally, and for which it is desired that at least part of the release takes place while the composition is located in the intestines.

The content of the active substance in the matrix may vary within wide limits. Many active substances may thus suitably be present in an amount of up to about 60%, typically up to about 50%, by weight of the composition. An active substance content of about 70% is contemplated to be the maximum content which still allows for a sufficient content of the crystalline polymer matrix, the surface active agent and the release modifier in the composition. The active substance may, on the other hand, be present in the composition in much smaller amounts, depending on the nature and strength of the active substance in question. The maximum quantity of any given active substance that may be incorporated into the matrix without having any adverse effect on the dissolution characteristics of the matrix will be able to be readily determined by a person skilled in the art.

The controlled release compositions may be produced by methods known per se in the art, e.g. using methods described in WO 89/09066, WO 91/04015 and WO 95/22962, or using other methods known either in the pharmaceutical industry or used in the production of polymer-based materials. One important advantage of the compositions of the invention is that they may be produced by relatively simple and inexpensive methods. For compositions without a coating, any suitable extrusion or injection moulding method and apparatus may be used. For compositions provided with a coating, non-limiting examples of suitable production methods include the following:

co-extrusion of a) the matrix material with the active substance dispersed therein and b) the coating;

injection moulding of the coating and subsequent injection moulding of the matrix containing the active substance;

injection moulding of the coating and subsequent injection moulding of alternating layers comprising at least one layer comprising matrix material and at least one layer comprising the active substance;

injection moulding of the matrix containing the active substance, or injection moulding of alternating layers comprising at least one layer comprising matrix material and at least one layer comprising the active substance, into a pre-formed tube which forms the coating;

extrusion or injection moulding of the matrix containing the active substance followed by dip coating.

In general, the components of the matrix, i.e. a crystalline polymer, a non-ionic emulsifier or other surface active agent and a release modifier, will be mixed while heating at a temperature sufficient to melt the polymer, and while stirring, so as to obtain a substantially homogeneous mixture. The active substance may be added to this mixture before or after heating, as appropriate. The molten mixture is then e.g. extruded or injected. For the preparation of a composition for pulsatile release of the active substance, the active substance may conveniently be included in matrix material, the mixture of the active substance and the matrix material being e.g. extruded or injected in layers which alternate with layers of the matrix without the active substance.

It will be clear to persons skilled in the art that the amount of active substance and the dimensions and specific form of the composition of the invention will vary according to the nature of the active substance in question as well as the intended use of the composition. The particular dose of the active substance to be administered to a person or animal will thus depend on such factors as the condition and age of the patient and the particular condition being treated.

DESCRIPTION OF THE DRAWINGS

FIG. 1 shows the release for compositions prepared according to Example 2 below.

FIG. 2 shows the release for compositions prepared according to Example 5.

The invention will be further illustrated in the following non-limiting examples.

EXAMPLES

In the examples below, all percentages are by weight.

Preparation of Controlled Release Compositions

The general method for preparation of the controlled release compositions described below is as follows:

The PEG 35,000 is mixed for 1 minute in a high speed dry mixer (Robot Coupe) at medium speed. The other ingredients, with the exception of PEG 2000 monostearate and microcrystalline wax, are then mixed together and added to the high speed dry mixer, where they are mixed with the PEG at medium speed for 1 minute. The PEG 2000 monostearate and, where applicable, microcrystalline wax are melted on a heating plate at a temperature of 100-150° C. and then added to the mixture of the other ingredients while mixing at low speed. After mixing for 70 seconds, the bottom and sides of the mixer are scraped with a spatula to obtain a homogeneous mixture, and mixing is performed for another 20 seconds at low speed. The mixture is then allowed to cool to room temperature and is ready to be fed into an injection moulding machine.

The compositions were prepared by injection moulding (Arbourg Allrounder) using a single unit mould, resulting in a composition containing a cylindrical inner matrix with dimensions of 4×12 mm. They were provided with a cylindrical coating having a maximum thickness of 0.4 mm.

Test Methods

The compositions described below were tested using a dissolution test method and apparatus as described in USP 23, NF 18 (The United States Pharmacopeia, 1995). The test apparatus (Erweka instrument equipped with 6 vessels) corresponds to "apparatus 2" described in USP 23, i.e. employing a paddle stirring element. The test method involves placing a test composition in a vessel with an acidic pH of 2.0 and agitation at 150 RPM for a period of 4 hours, after which the composition is transferred to another vessel with a neutral pH of 7.2 and agitation at 30 RPM. The composition remains in this vessel with neutral pH and low agitation for the remainder of the test. The buffers are as specified by USP, i.e. a KCl/HCl buffer for pH 2.0 and a phosphate buffer for pH 7.2. The two vessels approximate the conditions of the stomach and intestines, respectively, in terms of pH, agitation (peristaltic movements) and residence time. In the examples below, dissolution of the compositions is determined using a colourimetric method based on tartrazine colouring.

Example 1 (Comparative Example)

Controlled release matrix compositions were prepared from the following ingredients:

| | |
|---|---|
| PEG 35,000 | 40% |
| Potato starch | 46% |
| Ethylcellulose (Ethocel 50 M) | 3% |
| Tartrazine | 1% |
| PEG 2000 monostearate | 10% |

The compositions were tested as described above. At 150 RPM, pH 2.0, 100% of the matrix had eroded in less than the 4 hours stipulated by the USP (average 3.5 hours). At 30 RPM, pH 7.2, the matrix eroded in 11 hours in a zero order fashion.

Example 2

Controlled release matrix compositions were prepared from the following ingredients:

| | |
|---|---|
| PEG 35,000 | 32% |
| Nifedipin | 55% |
| Tartrazine | 1% |
| Cholesterol | 2% |
| AQOAT* | 3% |
| PEG 2000 monostearate | 7% |

Figure 1:
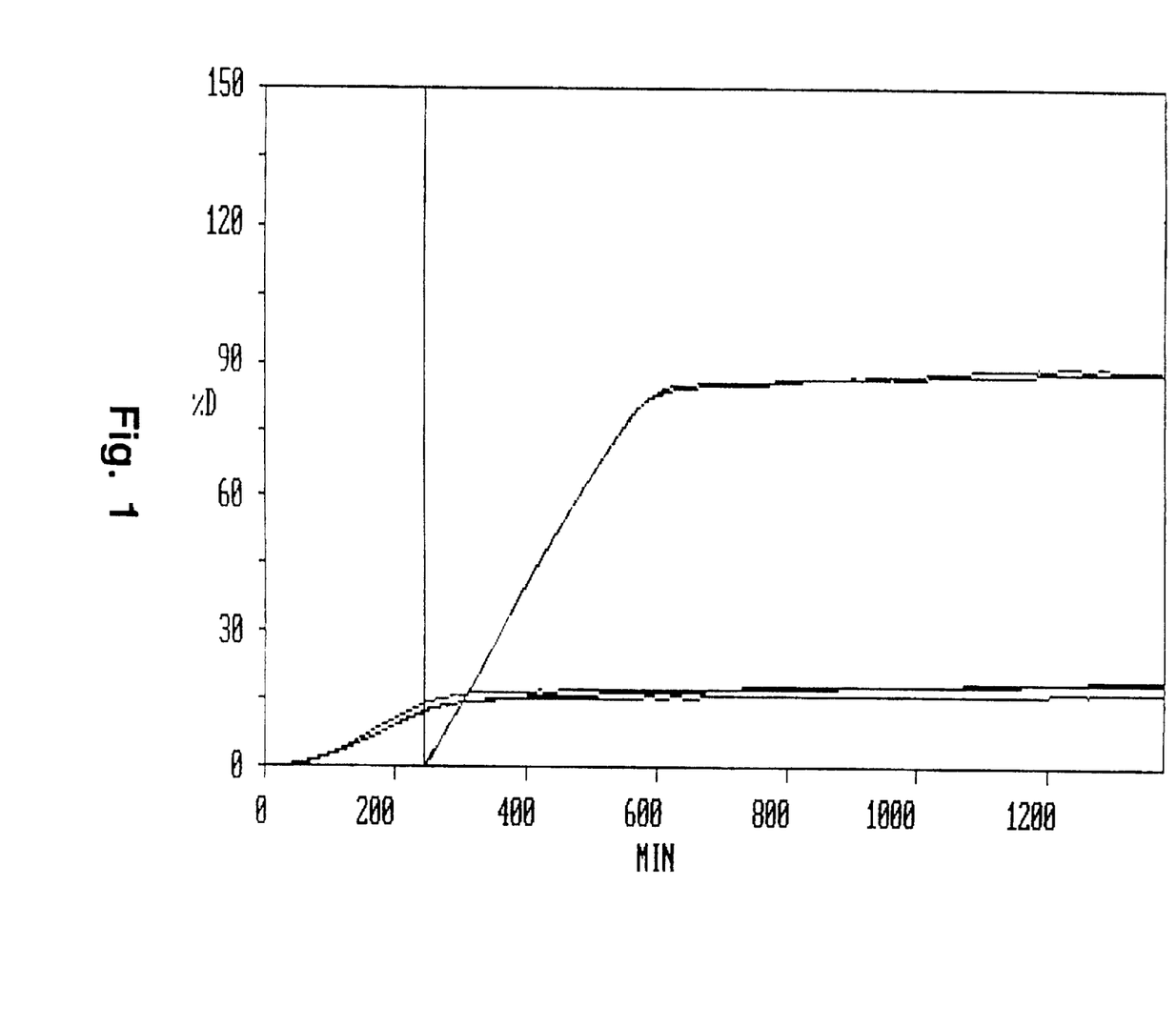
FIGS. 1 and 2 show the release profiles for selected compositions according to the invention tested as described below, i.e. at a pH of 2.0 and agitation at 150 RPM for a period of 4 hours followed by a pH of 7.2 and agitation at 30 RPM for the remainder of the test. In both figures, the release profiles starting at time=0 show the release as measured during the first 4 hours at acidic pH and high agitation, whereas the release profiles starting at time=240 min. show the release for the remainder of the test after the compositions have been transferred to a vessel with neutral pH and low agitation. The vertical line at time=240 min. indicates the point at which the compositions were transferred from the first (acidic) vessel to the second (neutral) vessel. It should be noted that for the acidic release profiles starting at time=0, only the release for the first 4 hours is relevant, the remaining part of the curves being simply the result of ongoing automatic measurements in the first vessels.

*Hydroxypropyl methylcellulose acetate succinate from Shin-Etsu Chemical Co., Japan The composition gave substantially zero order release over a period of about 10 hours. The release profile of this composition is shown graphically in FIG. 1.

Example 3

Controlled release compositions were prepared from the following ingredients:

| | |
|---|---|
| PEG 35,000 | 29.5% |
| Nifedipin | 55% |
| Tartrazine | 1% |
| Microcrystalline wax | 3% |
| AQOAT | 5% |
| PEG 2000 monostearate | 6.5% |

Due to the relatively large amount of the release modifier in this composition, no release of the active ingredient was obtained in an acidic environment. Dissolution of the composition in a neutral environment took place over a period of about 10 hours.

Example 4

Controlled release compositions were prepared from the following ingredients:

| | |
|---|---|
| PEG 35,000 | 32% |
| Nifedipin | 55% |
| AQOAT | 2.5% |
| Tartrazine | 1% |
| Ethyl cellulose | 2.5% |
| PEG 2000 monostearate | 7% |

This composition gave a substantially zero order release over a period of about 10-11 hours.

Example 5

Controlled release compositions were prepared from the following ingredients:

| | |
|---|---|
| PEG 35,000 | 30.4% |
| Nifedipin | 55% |
| AQOAT | 3% |

-continued

| | |
|---|---|
| Sorbic acid | 5% |
| PEG 2000 monostearate | 6.6% |

Figure 2:
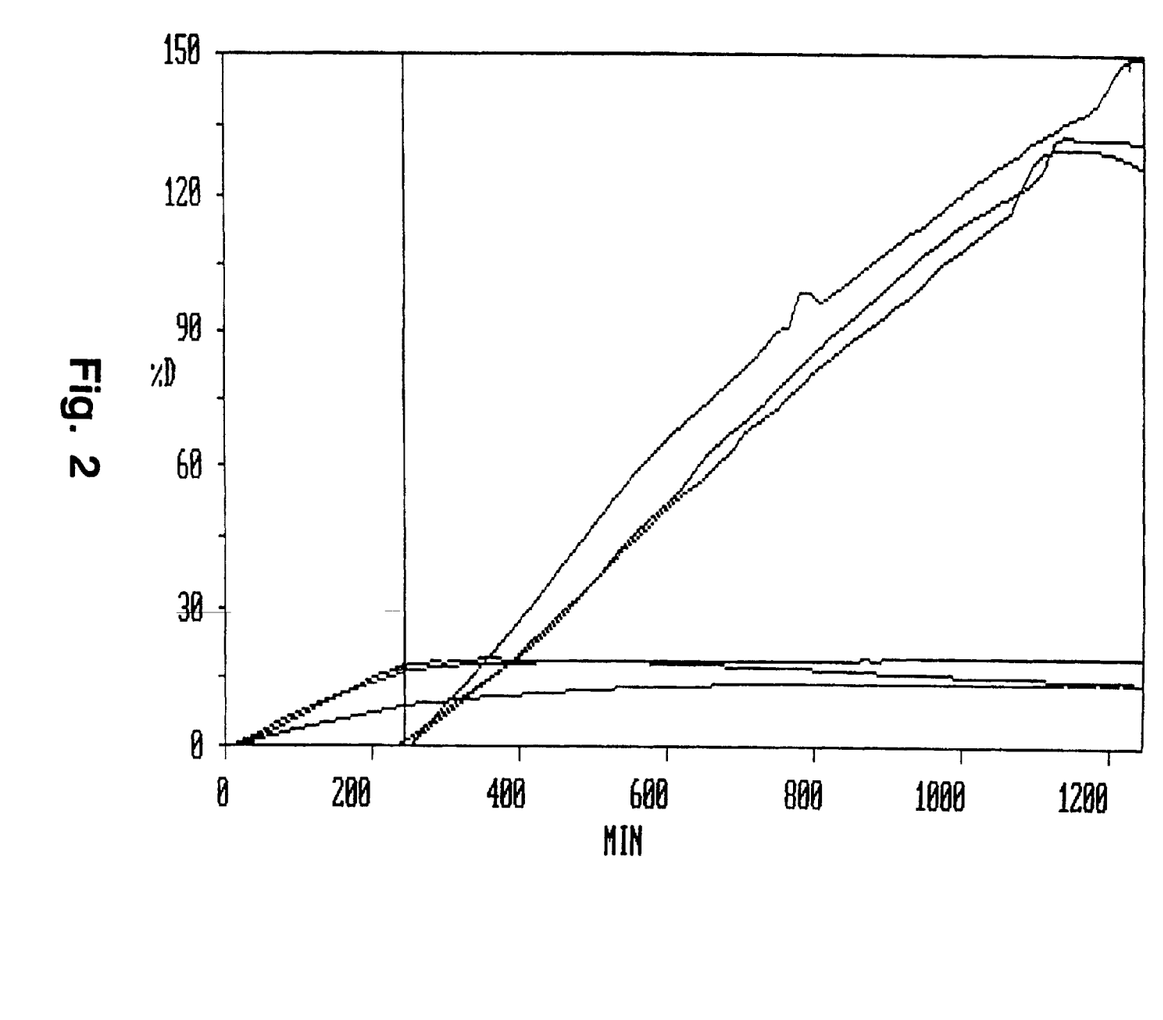

This composition provided a substantially zero order release over a period of about 18 hours. The release profile of the composition is shown graphically in FIG. 2.

The invention claimed is:

1. A composition for controlled delivery of at least one drug into an aqueous medium by erosion at a preprogrammed rate of at least one surface of the composition, the composition comprising
(A) a matrix which is erodible in the aqueous medium in which the composition is to be used and which allows substantially no diffusion of water into the composition beyond any exposed surface layers of the matrix,
wherein the matrix comprises, substantially homogeneously distributed in the matrix,
(i) at least one drug,
(ii) at least one substantially water soluble crystalline polymer with at least one water-dispersible or water-soluble surface active agent dispersed therein, and
(iii) at least one material that is water soluble at a pH in the range of from about 5 to about 7 and substantially water-insoluble at lower pH values, wherein the material is selected from the group consisting of polyvinyl acetate phthalate, hydroxypropyl methylcellulose phthalate, and hydroxypropyl methylcellulose acetate succinate copolymers, wherein the material is present in an amount of about 0.1-10%, based on the weight of the matrix, and provides the composition with a pH-dependent release of the at least one drug, and
(B) a coating on the matrix having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled.

2. A composition according to claim 1, wherein release of the drug is adapted so that the release rate in an in vitro environment approximating the environment of the human stomach with respect to peristaltic movements and pH is not substantially greater than the release rate of the drug in an in vitro environment approximating the environment of the human intestines with respect to peristaltic movements and pH.

3. A composition according to claim 1, wherein the matrix comprises a crystalline polyethylene glycol polymer having dispersed therein at least one non-ionic emulsifier.

4. A composition according to claim 1, wherein the coating comprises:
(a) a first cellulose derivative which has thermoplastic properties and which is substantially insoluble in the aqueous medium in which the composition is to be used wherein the first cellulose derivative is selected from the group consisting of ethylcellulose having an ethoxyl content in the range of 44.5-52.5%, cellulose acetate, cellulose propionate and cellulose nitrate;
and at least one of:
(b) a second cellulose derivative which is soluble or dispersible in water, wherein the second cellulose derivative is selected from the group consisting of methylcellulose, carboxymethylcellulose and salts thereof, microcrystalline cellulose, ethylhydroxyethylcellulose, ethylmethylcellulose, hydroxyethylcellulose, hydroxyethylmethylcellulose, hydroxypropyl cellulose, hydroxypropylmethylcellulose, hydroxymethylcellulose and hydroxymethylpropylcellulose;
(c) a plasticizer; and
(d) a filler.

5. A composition according to claim 4, wherein the coating further comprises an enteric coating material that functions to regulate erosion of the matrix within a pH of from about 2 to about 7.

6. A composition according to claim 5, wherein the concentration of the enteric coating material in the coating is greater than the concentration of material (iii) in the matrix.

7. A composition according to claim 1, wherein the matrix comprises different zones, and wherein the composition has been adapted to compensate for differential absorption in the gastrointestinal tract by varying the concentration of the material (iii) or the drug in different zones of the matrix.

8. A composition according to claim 1, wherein the matrix comprises at least two matrix zones having different concentrations of drug.

9. A composition according to claim 8, comprising different drugs in the different matrix zones of the composition.

10. A composition according to claim 1, further comprising at least one remote zone comprising a drug, optionally dispersed in a filler, such that the remote zone becomes exposed to the aqueous medium after a predetermined period of at least about 15 minutes after administration of the composition.

11. A method for producing a composition for controlled delivery of at least one drug into an aqueous medium by erosion at a preprogrammed rate of at least one surface of the composition, the method comprising forming a matrix which is erodible in the aqueous medium in which the composition is to be used and which allows substantially no diffusion of water into the composition beyond any exposed surface layers of the matrix, comprising mixing to substantial homogeneity:
(i) at least one drug,
(ii) at least one substantially water soluble crystalline polymer with at least one water-dispersible or water-soluble surface active agent dispersed therein, and
(iii) at least one material that is water soluble at a pH in the range of from about 5 to about 7 and substantially water-insoluble at lower pH values, wherein the material is selected from the group consisting of polyvinyl acetate phthalate, hydroxypropyl methylcellulose phthalate, and hydroxypropyl methylcellulose acetate succinate copolymers, wherein the material is present in an amount of about 0.1-10%, based on the weight of the matrix, and provides the composition with a pH-dependent release of the at least one active substance.

12. A method according to claim 11, wherein the matrix is formed using means that include extrusion, injection moulding, blow moulding or compression moulding.

13. A composition according to claim 1, wherein release of the drug is adapted so that the release rate in an in vitro environment approximating the environment of the human stomach with respect to peristaltic movements and pH is not greater than the release rate of the drug in an in vitro environment approximating the environment of the human intestines with respect to peristaltic movements and pH as described herein.

14. A composition according to claim 3, wherein the coating comprises:
(a) a first cellulose derivative which has thermoplastic properties and which is substantially insoluble in the aqueous medium in which the composition is to be used, wherein the first cellulose derivative is selected from the group consisting of ethyl cellulose having an ethoxyl content in the range of 44.5-52.5%, cellulose acetate, cellulose propionate and cellulose nitrate;

and at least one of:
(b) a second cellulose derivative which is soluble or dispersible in water, wherein the second cellulose derivative is selected from the group consisting of methylcellulose, carboxymethylcellulose and salts thereof, microcrystalline cellulose, ethylhydroxyethylcellulose, ethylmethylcellulose, hydroxyethylcellulose, hydroxyethyl methylcellulose, hydroxypropylcellulose, hydroxypropylmethylcellulose, hydroxymethylcellulose and hydroxymethylpropylcellulose;
(c) a plasticizer; and
(d) a filler.

15. A composition for controlled delivery of at least one drug into an aqueous medium by erosion at a preprogrammed rate of at least one surface of the composition, the composition comprising
(A) a matrix which is erodible in the aqueous medium in which the composition is to be used and which allows substantially no diffusion of water into the composition beyond any exposed surface layers of the matrix, wherein the matrix comprises, substantially homogeneously distributed in the matrix,
(i) at least one drug,
(ii) at least one substantially water soluble crystalline polymer with at least one water-dispersible or water-soluble surface active agent dispersed therein, and
(iii) at least one material that is water soluble at a pH in the range of from about 5 to about 7 and substantially water-insoluble at lower pH values, wherein the material is selected from the group consisting of polyvinyl acetate phthalate, hydroxypropyl methylcellulose phthalate, and hydroxypropyl methylcellulose acetate succinate copolymers, wherein the material is present in an amount of about 0.1-10%, based on the weight of the matrix, and provides the composition with a pH-dependent release of the at least one drug, and
(B) a coating on the matrix having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled, wherein the coating comprises (a) a first cellulose derivative which has thermoplastic properties and which is substantially insoluble in the aqueous medium in which the composition is to be used, wherein the first cellulose derivative is selected from the group consisting of ethylcellulose having an ethoxyl content in the range of 44.5-52.5%, cellulose acetate, cellulose propionate and cellulose nitrate;

and at least one of:
(b) a second cellulose derivative which is soluble or dispersible in water, wherein the second cellulose derivative is selected from the group consisting of methylcellulose, carboxymethylcellulose and salts thereof, microcrystalline cellulose, ethylhydroxyethylcellulose, ethylmethylcellulose, hydroxyethylcellulose, hydroxyethylmethylcellulose, hydroxypropylcellulose, hydroxypropylmethylcellulose, hydroxymethylcellulose and hydroxymethylpropylcellulose;
(c) a plasticizer; and
(d) a filler.

16. A composition for controlled delivery of at least one drug into an aqueous medium by erosion at a preprogrammed rate of at least one surface of the composition, the composition comprising
(A) a matrix which is erodible in the aqueous medium in which the composition is to be used and which allows substantially no diffusion of water into the composition beyond any exposed surface layers of the matrix, wherein the matrix comprises, substantially homogeneously distributed in the matrix,
(i) at least one drug,
(ii) at least one substantially water soluble crystalline polymer with at least one water-dispersible or water-soluble surface active agent dispersed therein, and
(iii) at least one material that is water soluble at a pH in the range of from about 5 to about 7 and substantially water-insoluble at lower pH values, wherein the material is selected from the group consisting of polyvinyl acetate phthalate, hydroxypropyl methylcellulose phthalate, and hydroxypropyl methylcellulose acetate succinate copolymers, wherein the material is present in an amount of about 0.1-10%, based on the weight of the matrix, and
(B) a coating on the matrix having at least one opening exposing at least one surface of the matrix, the coating being one which crumbles and/or erodes upon exposure to the aqueous medium at a rate which is equal to or slower than the rate at which the matrix erodes in the aqueous medium, allowing exposure of said surface of the matrix to the aqueous medium to be controlled, wherein the coating comprises
(a) a first cellulose derivative which has thermoplastic properties and which is substantially insoluble in the aqueous medium in which the composition is to be used, wherein the first cellulose derivative is selected from the group consisting of ethylcellulose having an ethoxyl content in the range of 44.5-52.5%, cellulose acetate, cellulose propionate and cellulose nitrate;

and at least one of:
(b) a second cellulose derivative which is soluble or dispersible in water, wherein the second cellulose derivative is selected from the group consisting of methylcellulose, carboxymethylcellulose and salts thereof, microcrystalline cellulose, ethylhydroxyethylcellulose, ethylmethyl cellulose, hydroxyethylcellulose, hydroxyethylmethylcellulose, hydroxypropylcellulose, hydroxypropylmethylcellulose, hydroxymethylcellulose and hydroxymethylpropylcellulose;
(c) a plasticizer; and
(d) an enteric coating material that functions to regulate erosion of the matrix within a pH of from about 2 to about 7 the material (iii) of the matrix and the enteric coating material (d) providing the composition with a pH-dependent release of the at least one active substance.

* * * * *